United States Patent

Wardley et al.

[11] Patent Number: 6,013,506
[45] Date of Patent: Jan. 11, 2000

[54] FELINE LEUKEMIA VIRUS VACCINES

[76] Inventors: Richard C. Wardley, 15216 Marshfield Rd., Hickory Corners, Mich. 49060; Darrell R. Thomsen, 6916 Wilson Dr., Kalamazoo, Mich. 49009

[21] Appl. No.: 08/461,920

[22] Filed: Jun. 5, 1995

Related U.S. Application Data

[63] Continuation of application No. 08/256,453, filed as application No. PCT/US92/08427, Oct. 8, 1992, which is a continuation of application No. 07/857,064, Mar. 25, 1992, abandoned, which is a continuation-in-part of application No. 07/789,163, Nov. 8, 1991, abandoned.

[51] Int. Cl.[7] .............................. C12N 7/00; A61K 39/21; A61K 39/12; C07K 1/00
[52] U.S. Cl. .................................. 435/235.1; 424/187.1; 424/199.1; 424/207.1; 530/395; 530/826; 930/221
[58] Field of Search ...................... 435/235.1; 424/187.1, 424/207.1, 199.1; 530/395, 826; 930/221

[56] References Cited

U.S. PATENT DOCUMENTS

| | | | |
|---|---|---|---|
| 4,745,051 | 5/1988 | Smith et al. | 435/68 |
| 4,748,019 | 5/1988 | Lysons | 424/262.1 |
| 4,876,089 | 10/1989 | Luciw et al. | 424/89 |
| 5,352,449 | 10/1994 | Beltz et al. | 424/187.1 |

FOREIGN PATENT DOCUMENTS

| | | | |
|---|---|---|---|
| 0173997 | 3/1986 | European Pat. Off. | C12N 15/00 |
| 0216564 | 4/1987 | European Pat. Off. | C12N 15/00 |
| 0247904 | 12/1987 | European Pat. Off. | A61K 39/21 |
| 61-500662 | 11/1984 | Japan | C07K 15/12 |
| 2181435 | 4/1987 | United Kingdom | C12N 15/00 |
| 9001547 | 2/1990 | WIPO | C12N 15/10 |
| 9100341 | 6/1990 | WIPO | C12N 5/06 |
| 9100341 | 1/1991 | WIPO | C12N 5/06 |
| 9107425 | 5/1991 | WIPO | C07K 1/00 |

OTHER PUBLICATIONS

Noteborn, M.H.M., et al, *J. Gen. Virol.*, 71:2641–2648 (1990).
Wells, D.E., and Compans, R.W., *Virology*, 176:575–586 (1990).
Hu, S–L, et al, *J. Virol.*, 61:3617–3620 (1987).
Rusche, J.R., et al, *Proc. Natl. Acad. Sci. U.S.A.*, 84:6924–6928 (1987).
Morikawa, S., et al, *Virology*, 183:288–297 (1991).
Luo, L., et al, *Virology*, 179:874–880 (1990).
Gheysen, D., et al, *Cell*, 59:103–112 (1989).
Overton, H.A., et al, *Virology*, 170:107–116 (1989).
Hu, S–L, et al, *J. Virol.*, 61:3617–3620 (1987).
Madisen, L., at al, *Virology*, 158:248–250 (1987).
Delchambre, M., et al, *EMBO*, 8:2653–2660 (1989).
Rasmussen, L., et al, *Virology*, 178:435–451 (1990).
Kimman, T. G., et al, *Veterinary Immunology & Immunopathology*, 22:145–160 (1989).
Cole, G., et al., *J. Virol*, 64:4930–4938 (1990).
Liew, F. Y, et al., *Eur. J. Immunol.*, 14:350–356 (1984).
Luckow, V. A., et al., *Bio/Technology*, 6:47–55 (1988).
Thomsen, D., *J. Gen. Virol.*, 73:1819–1824 (1992).
Wardley, R., et al., *J. Gen. Virol.*, 73:1811–1818 (1992).
Cole et al. (1990) J. Virology 64, 4930–4938.
Luckow et al. (1988) Bio/Technology 6, 47–55.
Gheysen et al. (1989) Cell 59, 103–112.

*Primary Examiner*—Jeffrey Stucker
*Assistant Examiner*—Hankyel T. Park
*Attorney, Agent, or Firm*—James D. Darnley, Jr.; Mark Deluca

[57] ABSTRACT

Disclosed are recombinant baculovirus expressing the gag, gp70, and gp85 genes of feline leukemia virus. Also disclosed are vaccines based on protein expressed from these recombinants. Also disclosed is a combined mucosal/parenteral inoculation method.

20 Claims, 4 Drawing Sheets

CONTACT CHALLENGE

WEEKS POST CHALLENGE

FELINE LEUKEMIA VIRUS VACCINES

This application is a continuation of U.S. Ser. No. 08/256,453, filed May 5, 1994, abandoned; which was filed as International Patent Application No. PCT/US92/08427, filed Oct. 8, 1992; which is a continuation of U.S. Ser. No. 07/857,064, filed Mar. 25, 1992, abandoned; which is a continuation-in-part of U.S. Ser. No. 07/789,163, filed Nov. 8, 1991, abandoned.

FIELD OF THE INVENTION

Disclosed are recombinant baculovirus expressing the gag, gp70, and gp85 genes of feline leukemia virus, vaccines, and methods of making and using vaccines based on these expressed products. Also disclosed is a combined mucosal/parenteral inoculation method.

BACKGROUND OF THE INVENTION

Feline Leukemia Virus

The oncomovirus feline leukemia virus (FeLV) is a member of the Retroviridae family of viruses. In cats, FeLV can cause lymphoma, myeloproliferative diseases, leukemia, immunodeficiency syndrome, aplastic anemia, and neurological disease. The virus is highly infectious for newborn or young kittens while older cats are resistant to even the most oncogenic strains of FeLV. Animals can be vaccinated against FeLV. For instance, early attempts to produce a vaccine for FeLV infection included the administration of live or inactivated FL74 feline lymphoma cells using a variety of adjuvants. However the efficacy of these vaccines has been disputed and many of these attempts were unsuccessful in protecting cats either against persistent viraemia or secondary lymphoma and sarcoma development. Soluble tumor cell antigen vaccines are presently commercially available and other experimental vaccines based on ISCOMs and subunits have also been reported.

The FeLV genome codes for three genes: a gag gene coding for the major structural components of the virus, an env gene which codes for the envelope glycoprotein, and a pol gene encoding the polymerase protein. The gag gene is expressed as a 65 kD polyprotein which is processed into four subunits: a p15 matrix protein, a p12 protein of unknown function, a p27 capsid protein, and a p10 nucleocapsid protein. The pol gene encodes three proteins: the protease, reverse transcriptase and the integrase. Autoprocessing by the protease portion of the gene gives rise to all three proteins of the pol region. Additionally, the protease is responsible for the processing of the gag precursor. The pol gene is expressed as a gag-pol fusion protein. The envelope gene is expressed as a 85 Kd glycoprotein, gp85, which is further processed to the disulfide bound, membrane associated 70 kD and 15 kD (p15E) complex found on the surface of the virion. This same gag-protease region has been inserted into the feline herpes virus (FHV) genome and shown to produce both the gag gene product and a gag-protease fusion protein in recombinant FHV infected cells. The protease was also active in processing the gag (p65) into its four polypeptide components.

Baculovirus Expression System

Baculoviruses are a large group of viruses which are highly virulent to specific insects but are not pathogenic to vertebrates or plants. With the advent of the baculovirus expression vector system (BEVS) a wide variety of genes of viral, fungal, bacterial, plant, and animal origin have been expressed in recombinant baculovirus. Briefly, BEVS uses expression vectors to insert heterologous genes into the baculovirus genome at a location such that the gene will be expressed under the control of the baculovirus regulatory elements. The recombinant baculovirus is allowed to infect a cultured insect cell line, where the heterologous protein is expressed. Several groups using this system have expressed the surface glycoprotein of two other retroviruses, human immunodeficiency virus and avian leukemia virus. Reportedly, the retroviral gag gene has also been expressed and been found to be assembled into virus-like particles in the infected insect cells.

Vaccination

Vaccination of mammals is nearly always done via the use of subcutaneous or intramuscular injection, with subcutaneous being the preferred route. In the case of small companion animals (dogs, cats, etc.) some vaccines are also administered intranasally and/or orally. Administration of vaccines to a host in these two distinct ways is disadvantageous as the immune system response is compartmentalized. This means that subcutaneous administration only really stimulates a systemic response whereas inoculation at a mucosal surface is geared to the stimulation of that distinct immunological department.

We describe here the construction of recombinant baculoviruses that not only express the gag, gp70, and gp85 genes of FeLV, but also assemble immature virus-like particles which are shed into the medium of insect cells coinfected with both the gag and gp85 viruses. In addition, the present invention provides means for making such viruses, and FeLV vaccines based on these recombinant viruses. The invention also includes methods of vaccinating a mammal and we have found, surprisingly, that by administration of a vaccine to both mucosal and systemic sites in the natural viral host, essentially full protection against persistent viraemia can be achieved.

Information Disclosure

Noteborn, M. H. M., et al, *J. Gen. Virol.* 71:2641–2648 (1990), report the expression of surface glycoprotein of avian leukemia virus in insect cells using BEVS. This reference does not suggest the recombinant baculovirus of the invention.

Wells, D. E., and Compans, R. W., *Virology* 176:575–586 (1990), Hu, S-L, et al, *J. Virol.* 61:3617–3620 (1987), and Rusche, J. R., et al, *Proc. Natl. Acad. Sci. U.S.A.* 84:6924–6928 (1987), report the expression of surface glycoprotein of human immunodeficiency virus (HIV) in insect cells using BEVS. These reference do not suggest the FeLV recombinant baculovirus of the invention.

Morikawa, S., et al, *Virology* 183:288–297 (1991), report the use of BEVS in the expression of the gag gene from the lentivirus feline immunodeficiency virus (FIV). The expressed protein assembles into virus like particles (VLPs) in infected insect cells when cotransfected as a gag sequence. Inclusion of the pol sequence abolished particle formation. The reference does not suggest the FeLV recombinant baculovirus of the invention.

Luo, L., et al, *Virology* 179:874–880 (1990), Gheysen, D., et al, *Cell* 59:103–112 (1989), Overton, H. A., et al, *Virology* 170:107–116 (1989), Hu, S-L, et al, *J. Virol.* 61:3617–3620 (1987), and Madisen, L., at al, *Virology* 158:248–250 (1987), report the expression of the lentivirus human immunodeficiency virus (HIV) gag protein assembled into virus-like particles in infected insect cells. The expressed protein assembles into virus like particles in infected insect cells when cotransfected as a gag sequence. However, again, including the pol sequence abolished the VLPs.

Delchambre, M., et al, *EMBO* 8:2653–2660 (1989), report the expression of the lentivirus simian immunodeficiency virus (SIV) gag protein assembled into virus-like particles in infected insect cells. The expressed protein assembles into virus like particles in infected insect cells when cotransfected with a gag sequence. However, including the pol sequence abolished the VLPs and, thus, this reference does not suggest the FeLV recombinant baculovirus of the invention.

Rasmussen, L., et al, *Virology* 178:435–451 (1990), report the expression of the lentivirus bovine immunodeficiency virus (BIV) gag protein assembled into virus-like particles in infected insect cells. The expressed protein assembles into virus like particles in infected insect cells when cotransfected with the gag sequence. However, including the pol sequence abolished the VLPs and, thus, this reference does not suggest the FeLV recombinant baculovirus of the invention.

Kimman, T. G., et al, *Veterinary Immunology & Immunopathology* 22:145–160 (1989) report on the effectiveness of a bovine respiratory syncytial virus vaccine given via a mucosal or intramuscular route. The report does not suggest administration at both sites in order to provide complete protection.

SUMMARY OF THE INVENTION

The present invention provides recombinant baculovirus comprising a DNA sequence encoding the immunogenic portion of the Feline leukemia virus (FeLV) genome. More particularly, the present invention provides recombinant baculovirus encoding gag, gp70, gp85, or the immunogenic portions thereof. Most particularly, the present invention provides recombinant AcNPV encoding gag, gp70, gp85, or the immunogenic portions thereof.

The present invention also provides host cells and cell cultures infected with a recombinant baculovirus, the recombinant baculovirus comprising a DNA sequence encoding the feline leukemia virus (FeLV) genes gag, gp70, gp85, or the immunogenic portions thereof.

In addition, the invention provides gag, gp70, and gp85 protein, or the immunogenic portions thereof, produced by the recombinant baculovirus or host cells and cell cultures infected with the recombinant baculovirus of the invention.

The present invention further provides recombinant baculovirus vaccines and methods of protecting animals from FeLV infection by vaccinating them with these vaccines.

A second aspect of the invention provides a combined mucosal/parenteral inoculation method comprising a first inoculation via mucosal administration of a vaccine, followed by a second inoculation via parenteral administration of the same or different vaccine.

More particularly, this aspect of the invention provides a combined mucosal/parenteral inoculation where the first inoculation is nasal and the second is intramuscular.

Most particularly, the invention provides mucosal administration of FeLV vaccine to a cat, followed by subcutaneous administration of gag or gp85 protein produced by the recombinant baculovirus of the invention.

An additional aspect of the combined mucosal/parenteral inoculation method provides immunization kits suitable for use in the method of the invention.

BRIEF DESCRIPTION OF THE FIGURES

FIG. 8 shows the results of the p27 assay results at 9 weeks post-challenge from sera of cats vaccinated with different vector combinations where each bar represents value from one cat (Vaccine Experiment III) and values in the shaded portion are considered negative.

DETAILED DESCRIPTION OF THE INVENTION

Any immunogenic FeLV protein may be expressed in baculovirus following the methods and techniques described here. For instance, the location and sequences of the genes encoding gag, gp70, and gp85, of FeLV as well as the protein sequences encoded thereby, are known and may be isolated following techniques well known in the art See for example, U.S. Pat. 4,789,702 (sequence of FeLV gp70); EP 0 247 904 (peptide sequence of gp70), *J. Virol.* 62:722–731 (gp85). Alternatively, and using these published sequences for gag, gp70, and gp85, the gene may be chemically synthesized using an apparatus designed for this purpose following techniques well known in the art. Using recombinant techniques the genes encoding gag, gp70, and gp85, or immunogenic portions thereof, of FeLV have been transformed into plasmids and thus the genes can be conveniently, and in the transfer vectors of the invention preferably are, obtained from such a source. Exemplary plasmids are pFeLVgag3 (encoding the gag gene), pTC2 (encoding gp85) (also known as PUC-FeLVenv), ptGAΔAvaI, ptGAΔApaI, pt9:3-19 (all encoding antigenic portions of gp70 as reported in U.S. Pat. No. 4,701,416); pFeLVgag3 and pTC2 are preferred in the embodiments of the invention.

BEVS is also well known in the art as a convenient recombinant expression system which in some cases has been shown to produce large quantities of heterologous protein. BEVS is reviewed in detail by Luckow, V. A., Cloning and expression of heterologous genes in insect cells with baculovirus vectors. In: Recombinant DNA Technology and Applications. Eds. C. Ho, A. Prokop, and R. Bajpai (1990) McGraw-Hill, New York, and Luckow, V. A. & Summers, M. D., *Bio/Technology* 6:47–55 (1988), which are incorporated by reference. For the construction of the recombinant baculovirus of the invention we use the method described in detail in the latter publication.

While there are a large number of baculovirus species known, the preferred virion for use in BEVS are *Autographa californica* nuclear polyhedrosis virus, also known as AcNPV or AcMNPV. AcNPV infects over 30 varieties of Lepidoptera cells, the preferred host being the *Spodoptera frugiperda* cell line Sf9.

The foreign genes to be inserted into baculovirus use plasmids which contain a cloning site flanked by baculovirus DNA. The cultured host cell is cotransfected with this plasmid and genomic wild-type baculovirus DNA, which recombines to produce a viral genome carrying the heterologous gene. The methods and conditions by which cotransfection occurs are well known in the art. Examples include calcium phosphate co-precipitation (Graham, F. L. and van der Eb, A. J., *Virology* 52:456–467 (1973)), protamine (Wienhues, U., et al, *DNA* (*NY*) 6:81–89 (1987)), lipopectin (*Biotechniques* 11:310–312) and electroporation (Mann, S. G. and King, L. A., *J. Gen. Virology* 70:3501–3505 (1989)). We use the calcium phosphate method, outlined in more detail below, which is the preferred transfection method to produce the recombinant baculovirus of the invention.

Typically, the heterologous gene is targeted for insertion into the polyhedron gene, a gene which is not essential for replication or production of extracellular virus. This is generally accomplished by including in the plasmid transfer vector baculovirus DNA encoding the polyhedron promoter and sequences of 3' and 5' DNA flanking the polyhedron promoter. Foreign genes are then inserted into the transfer vector downstream of the promoter using recombinant DNA techniques known in the art. A wide variety of suitable transfer vectors are known and would be suitable for use in embodiments of the invention. Among these are pACYMI, pEV55, pAC373, pACRP, pEVIV, pEV51, and pVL941; the preferred vector is pVL941. Further, both the gag and env genes could be inserted into a single virus using several of the multiple cloning site vectors which are available. Examples of suitable multiple site vectors include p2XIVVI⁻X3, pXIVVI⁻, pSyn nWTVI⁻ (as described in *Gene* 100:131–137 (1991)), or pACVC2, as described in *Protein Engineering* 1:359–366 (1987).

The recombinant baculovirus of the invention can be identified by visual screening followed by DNA dot blot hybridization, cell affinity techniques, plaque hybridization, or other techniques known in the art. The recombinant baculovirus of the invention may also include proteins for which there are chromogenic and/or enzymatic substrates for ease of identification and purification. The preferred method is visual screening of recombinants since recombinants lack the occlusion bodies characteristic of wild-type baculovirus; visual screening is a technique which is well known in the art. The occlusion-lacking morpholytes are then picked and placed into a 96-well plate for DNA dot blot hybridization. This hybridization technique is well known in the art of recombinant DNA technology and requires no special mention. It is preferred to purify and more fully characterize several of the viruses corresponding to the strongest hybridization signals.

The recombinant baculovirus of the invention may be propagated in any number of continuously cultured insect cell lines, most typically *Anticarsa gemmitalis* (soybean caterpillar), *Bombyx mori* (silkworm), *Estigmene acrea* (saltmarsh caterpillar), *Heliothis virescens* (tobacco budworm), *Leucania separata, Lymantria dispar* (gypsy moth), *Malacasoma disstria* (forest tent caterpillar), *Mammestra brassicae* (cabbage worm), *Manduca sexta* (tobacco hornworm), *Plutella zylostella* (diamond-back moth), *Spodoptera exigua* (beet armyworm), and *Spodoptera littorlis*. The preferred insect cell line for the propagation of the recombinant baculovirus of the invention is *Spodoptera frugiperda* Sf-9.

A vaccine prepared utilizing a glycoprotein of the instant invention or an immunogenic fragment thereof can consist of fixed host cells, a host cell extract, or a partially or completely purified FeLV glycoprotein preparation from the host cells or produced by chemical synthesis. The FeLV glycoprotein immunogen prepared in accordance with the present invention is preferably free of intact FeLV virus. Thus, the vaccine immunogen of the invention is composed substantially entirely of the desired immunogenic FeLV polypeptide and/or other FeLV polypeptides displaying FeLV antigenicity.

The immunogen can be prepared in vaccine dose form by well-known procedures. The vaccine can then be administered parenterally or mucosally. For parenteral administration, such as intramuscular or subcutaneous injection, the immunogen may be combined with a suitable carrier, for example, it may be administered in water, saline or buffered vehicles with or without various adjuvants or immunomodulating agents including aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (Propionibacterium acnes), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.). Another suitable adjuvant is Freund's Incomplete Adjuvant (Difco Laboratories, Detroit, Mich.). Other vaccines may be prepared according to methods well known to those skilled in the art as set forth, for example, in I. Tizard, An Introduction to Veterinary Immunology, 2nd ed. (1982), which is incorporated herein by reference.

For parenteral administration the proportion of immunogen and adjuvant can be varied over a broad range so long as both are present in effective amounts. For example, aluminum hydroxide can be present in an amount of about 0.5% of the vaccine mixture ($Al_2O_3$ basis). On a per dose basis, and depending on the purity and immunogenicity of the antigen, the concentration of the immunogen can range from about 1.0 µg to about 100 mg per cat. The preferred concentration of immunogen and volume to be administered will vary depending on the age and weight of the host, as well as other factors known by those knowledgeable in the art of vaccination techniques. For example, in cats a preferable range is from about 10 µg to about 1.0 mg; a suitable dose size is about 0.5–5 ml, preferably about 1.0 ml. Accordingly, a dose for injection, for example, would comprise 1 ml containing 1.0 mg of immunogen in a mixture with 0.5% aluminum hydroxide. Comparable dose forms can also be prepared for parenteral administration to immature mammals, but the amount of immunogen per dose may be smaller, in kittens for example, about 0.25 to about 1.0 ml per dose.

For mucosal administration the immunogen may be combined with a suitable carrier, for example, water, saline, or buffered vehicles. In addition, various immunomodulating agents known in the art may be added to specifically enhance mucosal immune response. Such agents include cholera toxin or parts thereof, DEAE-dextran, interleukins (e.g. IL-5), LT toxin of *E. coli*, Shiga toxin, and other toxins from gram-negative organisms. Once formulated, such vaccines may be introduced at any mucosal surface, typically and most conveniently into the nares and/or oro-pharynx using devices suitable for this purpose e.g., dropwise with a small nasal cannula, by aerosolization, etc. The concentration of immunogen as well as dose size for mucosal administration is similar to that used for parenteral administration.

Vaccination may be accomplished following a two dose regime. Preferably, the two dose regimen comprises a first dose administered to a mucosal membrane, as outlined above, followed by a second dose administered parenterally. Following this aspect of the invention, the second dose is administered at some time following the first, mucosal, inoculation. The time period which should lapse between the first mucosal inoculation and the second later-in-time, parenteral, inoculation depends on the age, weight, health, etc. of the host, the virus against which protection is sought, the immunogenicity of the respective vaccines, etc. It is well recognized that, under normal conditions, the mucosal administration would comprise a replicating agent, i.e. live recombinant virus or bacteria, allowing antigens to gain access to the immune system. In addition, the second parenteral inoculation may consist of either a replicating or non-replicating agent. However, this protocol is not the exclusive mode of delivering an antigen as non-replicating antigens may be delivered to the mucosal immune system, e.g by microsphere encapsulation of antigens. These and other factors are well known in the art and the determination of the weight and relative importance of any of these factors is within the routine consideration of one skilled in the art. This dual procedure of the invention is most effective against viruses which show a compartmentalized immunogenic response i.e., viruses which gain entry into the host via a mucosal site but which also replicate systemically and is appropriate for use in all mammals, including humans. Examples of viral organisms which show such a compartmentalized response include those which cause influenza and herpes infections (in human); Infectious Rhinotracheitis and Viral Diarrhea (in bovine); Panleucopenia, Leukemia, Rhinotracheitis, and Calicivirus (in feline); Pseudorabies, Parvovirus, and Encepholomyocarditis viruses (porcine); Distemper, Infectious Hepatitis, and Parvovirus (canine). Examples of bacterial organisms include Staphylococcus infections in human, *Pasteurella multocida, P. hemolytica,* and *Hemophilus somnus* in bovine, *Actinobacillus pleuropneumonia, P. multocida* in porcine and *Bordetella bronchoseptica* in both porcine and canine. The dual procedure of the invention is also believed to be effective against organisms which replicate predominantly at either the mucosal site or the parenteral site, e.g. Respiratory Syncytial and Parainfluenza-3 viruses in bovine and Immunodeficiency virus in feline. Vaccines against these viruses are administered using dosages and concentrations suitable for each vaccine in the target animal and are known in the art. Vaccines currently available may need to be reformulated in order that they be made suitable for administration following this dual administration method of the invention.

This dual dose regime of the invention may also be accomplished by administering the two vaccine components simultaneously at their appropriate sites. Administration to both sites at precisely the simultaneous time is recognized by those skilled in the art to be unlikely and, thus, the time period for simultaneous administration includes the delay which may be experienced as, for example, the host is prepared for the second dose, the second dose is prepared for administration, the host is observed for signs of distress after the administration of the first dose, etc. Thus, when following the simultaneous administration method of the invention, a cat, for example, would receive a suitable dose of an appropriate vaccine formulation intranasally and/or orally and simultaneous intramuscular vaccination with an appropriate vaccine.

When vaccines are administered following the dual procedures of the invention the vaccines may contain the same immunogenic component manufactured or presented in the same or different vector or formulated in the same or different vehicle. It is believed that a simultaneous dual administration as just described provides stimulation to both immunogenic compartments and thus diminishes the need for the second, later-in-time, dose.

Vaccination with the FeLV vaccines of the inventions may also be accomplished following traditional regimes. Typically, a first dose is administered at a parenteral site or, more rarely in the case of some vaccines, at a mucosal site. The choice of site of first inoculation depends on the animal to be treated as well as the availability and suitability of the vaccine for that site. Following a suitable period of time, a second dose is administered if necessary. Traditionally, the second dose is administered at the same site as the first i.e., if the first is mucosal the second is mucosal. The decision as to which site is appropriate for initial administration, the need for and the period of time prior to a second dose, the dose to be given, etc., are all factors known and understood by one skilled in the art of mammalian vaccination.

For example when vaccinating cats, the first dose can be given at 6–10 weeks of age. The second dose of the vaccine then should be administered some weeks after the first dose, for example, about 2 to 4 weeks later. Alternatively, the vaccine can be administered as a single 1 ml dose, for example, at about 6–10 weeks of age. However, a two dose regimen is considered preferable for the most effective immunization of the cat. Annual revaccination is recommended. Adults may be revaccinated at any time. Kittens born to unvaccinated adults may be vaccinated at about 3–10 days, again at 4–6 months and yearly thereafter.

The FeLV vaccines of the invention, as well as known vaccines, when administered following traditional techniques or when administered following the dual method of the invention, may be combined with other vaccines for other diseases to produce multivalent vaccines. In addition, the vaccines of the invention, as well as known vaccines when administered following traditional techniques or when administered following the dual method of the invention, may also be combined with other medicaments, for example, antibiotics.

A "virus-like particle" is a particle produced by baculovirus infected insect cells which resembles an immature FeLV particle in density (upon chromatography) and in size, shape, and ring structure (upon EM analysis).

Most of the recombinant DNA methods employed in practicing the present invention are standard procedures, well known to those skilled in the art, and described in detail, for example, J. Miller, *Experiments in Molecular Genetics,* Cold Spring Harbor Laboratory, Cold Spring Harbor, N.Y. (1972), D. A. Morrison, *Transformation and Preservation of Competent Bacterial Cells by Freezing,* Methods Enzymol. 68:326–331 (1979), J. Sambrook, et al, *Molecular Cloning,* A Laboratory Manual, Cold Spring Harbor Laboratory Press (1989), J. Perbal, *A Practical Guide to Molecular Cloning,* John Wiley & Sons (1984), and M. D. Summers and G. E. Smith, Texas Agricultural Experimental Bulletin No. 1555 (1987), all of which are incorporated by reference. Except where noted, all restriction enzymes, chemicals, and materials, or their equivalents, are readily available from commercial vendors. Endonuclease restriction follows manufacturer recommendations.

Without further elaboration, it is believed that one skilled in the art can, using the preceding description, practice the present invention to its fullest extent. The following detailed examples describe how to construct the various recombinant baculovirus of the invention and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Materials and Methods

Cells, Viruses, and Plasmids

The parent baculovirus *Autographica californica* nuclear polyhedrosis virus (AcNPV), E2 strain, is obtained from Max Summers (Texas A & M University). The *Spodoptera frugiperda* cell line, Sf-9, is obtained from the American Type Culture Collection (CRL 1711). Plasmids pFeLVgag3, pTC2, and pCG113, and the cell line FeLV-A/FGA, were obtained from Cetus Corp. The cells, parent viruses, and recombinant viruses are propagated by methods described in detail in Texas Agricultural Experimental Bulletin No. 1555 (1987).

Plasmid pVL941 is described by Luckow, V. E. and M. D. Summers, *Virology* 170:31–39 (1989).

FeLV-A/FGA is a FeLV subgroup A persistently infected Crandell Feline Kidney (CRKF) cell line and is described in *J. Virol.* 64:4930–4938 (1990). FeLV-A/FGA cells are grown in Dulbecco's modified eagles medium (DMEM) supplemented with 10% fetal calf serum (FCS).

CT600 cells and Gp50 monoclonal antibody (MAB) are a gift from Dr. N. Pedersen, Davis, Calif.

AcNPV-gp50 is a recombinant baculovirus virus that expresses the envelope protein gp50 from pseudorabies virus and is synthesized following the protocol described in *J. Cell. Biochem.* 43:67–79 (1990).

FHV recombinants expressing gag and gp85 of FeLV are obtained from J. Nunberg of Cetus Corp. and expression is described in *J. Virol.* 64:4930–4938 (1990).

FeLV whole virus is produced in the FL74 cell line as described by Theilen et al., *Nature* 222:589–590 (1969). gp70 is prepared by using virus from FL74 cells purified as described in *Vaccine* 7:142–146 (1989).

Animals

Specific pathogen-free cats are used in all experiments. Animals are housed in a containment facility either in individual cages or in pens of 6–8 cats. Animals received cat food and water on an ad libitum basis.

Labelling of Virus Infected Cell Specific Polypeptides

Labelling with $^{35}$S-methionine (50 $\mu$CI/ml) is performed in Grace's medium plus 10% FCS containing one tenth the normal concentration of methionine. $^3$H-glucosamine (50 $\mu$Ci/ml) labelling is performed in Grace's medium plus 10% FCS. Yeastolate and lactalbumin hydrolysate are omitted from both labelling media. Cells are infected at a multiplicity of infection (MOI) of 5–10 plaque forming units (pfu)/ cell and labeled from 24 to 48 hours post infection. Methionine labelled cells and media are harvested and processed for immunoprecipitation as described in *J. Virol.* 60:216–223 (1986). Glucosamine labelled cells and media are harvested directly in SDS-PAGE dissociation buffer.

Sucrose Gradient Analysis

Sf-9 cells growing in 100 ml spinner flasks (1×10$^6$ cells/ml) are infected with the recombinant baculoviruses AcNPV-gag, AcNPV-gp85, AcNPV-gp70, or a control virus, AcNPV-gp50, at an MOI of 10 pfu/cell for singly infected cultures or 5 pfu/cell of each virus for doubly infected cultures. Infected cell cultures are harvested at 64 hours post infection. FeLV is harvested from the supernatant of persistently infected FeLV-A/FGA cells when the cells are confluent. Cells and cellular debris are removed by low speed centrifugation. The supernatant are then centrifuged at 100, 000×g for 1 hour. The pellets from these high speed spins are resuspended in phosphate buffered saline (PBS) and layered onto 20 to 60% sucrose gradients (in PBS) and centrifuged for 16 hours at 100,000×g in an SW41 rotor. Gradients are fractionated from the top. Each fraction (0.5 ml) is analyzed for sucrose concentration and protein content (BCA protein assay kit, Pierce Chemical Co.). Western blots are used to detect particular proteins in each fraction. The presence of virus particles in some fractions is observed directly by electron microscopy.

Western Blot Analysis

For western blot analysis, aliquots from each fraction of the gradients are separated on an 11% N,N-diallytartardiamide (DATD)-crosslinked polyacrylamide gel using the method of Laemmli (*Nature* 227: 680–685 (1970)). Following electrophoresis, proteins are electroblotted onto 0.22 um nitrocellulose following the procedure of Towbin, H., et al, *Proc. Natl. Acad. Sci. USA* 76:4350–4354 (1979). Unoccupied sites on the nitrocellulose are blocked by sequential incubation in PBS containing 0.1% Tween-20 and Tris-Saline, pH 7.4, containing 0.1% Brij-58. Blots are incubated with the primary antibody and color development carried out as described by Hink, W. F., et al, *Biotechnology Progress* 7:9–14 (1991). For detection of gag and gp70, monoclonal antibodies are used as described in Lutz, H., et al, *Am. J. Vet. Res.* 44:2054–2059 (1983), Lutz, H., et al, *Vet. Immunol. Immunopathol.* 2:425–440 (1981), and Grant, C. J., et al, *J. Immunol.* 131:3042–3048 (1983).

EM Analysis

Peak fractions from the sucrose gradients are prepared for EM by mixing 50 $\mu$l of the fraction with 100 $\mu$l of a 2% phosphotungstic acid (PTA) solution, pH 6.0, containing 0.05% bovine serum albumin (BSA) solution. The mixture is transferred as a single drop to a carbon-formvar coated grid (Ted Pella Inc., Redding, Calif.). The sample is allowed to adsorb for 30 seconds and excess fluid is removed by touching the edge of the grid to filter paper. Grids are observed at 60 KV on a JEOL 1200 transmission electron microscope.

Preparation of Antigen for Use as Vaccine

*Spodoptera frugiperda* (Sf-9) cells in spinner flasks are infected at a cell density of 1×10$^6$ cells/ml at a multiplicity of infection of 5 plague forming units (pfu)/cell. The cells are infected with the following recombinant viruses: either AcNPVgp85 or AcNPVgp70, or co-infected with AcNPVgp85 and AcNPVgag. Each culture is harvested at 72 hours post infection. Cells infected with gp85 or gp70 are tested as vaccines. Infected cells are separated from the culture medium by low speed centrifugation and stored frozen until used. Gag/gp85 particles are purified from 100 ml of the supernatant of infected cells by centrifugation at 100,000×g for 1 hour. The pellet from this procedure is resuspended in 5 ml PBS and stored frozen prior to formulation as a vaccine.

FHV recombinants expressing either FeLV gp70, gp85, or gag are grown in CRFK cells and harvested 3 days post-infection. After clarification to remove cell debris, supernatant fluid is titered and stored at −70° C. before use. Vaccine is formulated to contain 10$^5$–10$^7$ pfu/ml.

Laboratory Assays p27 levels in cats are measured using a commercially available kit (Synbiotics (San Diego, Calif.)). p27, a group-specific antigen of FeLV, is found in the blood of persistently-infected animals and hence can be used as a test for viraemia. Standardization in our laboratory indicated that within the context of known positive and negative sera, O.D. values of $\geq$0.25 are positive for viraemia.

FeLV specific antibodies are measured in two ELISAs against purified gp70 and purified whole virus. Gp70 is prepared by affinity chromatography using disrupted virus from FL74 cells (Theilen et al., *Nature* 222:569–570 (1969) and a gp70 monoclonal antibody. Column elutes are concentrated and used to coat ELISA plates at 2 µg protein/ml. After incubation for 18 hr at 4° C., plates are washed in phosphate buffered saline (PBS) before the addition of cat sera diluted 1:10 in PBS containing 0.05% Tween 20 (PBST). An appropriate dilution of horseradish peroxidase labelled anti-cat immunoglobulin (Kirkegaard and Perry, Gaithersburg Md., U.S.A.) is then reacted at room temperature with the plate for 45 min. After a further wash step, substrate and chromogen are added and color is allowed to develop before reading plates on an ELISA reader. Each plate contained appropriate negative and positive controls. Sera is tested in duplicate and increases in OD values of at least twice pre-treatment levels are scored as positive. Virus for the whole virus assay is prepared from FL74 cells by filtration through an Amicon filter and gradient centrifugation (*Vaccine* 7:142–146 (1989)). Material is stored at −20° C. and titrated with known positive and negative sera to find the appropriate dilution for use. Assays are run in a similar fashion to that described for gp70 antibody detection.

EXAMPLE 1
Expression of FeLV gag, gp85, and gp70

Cloning of gag Gene into Baculovirus Expression Vector

A 2.2 kB XbaI-EcoRI fragment is removed by endonuclease digestion from the plasmid pFeLVgag3. This fragment contains the coding sequences for the FeLV gag gene, as well as the protease portion of the pol gene (nucleotides 517–2786) (*J. Virol.* 62:722–731 (1988)). The ends of this fragment are repaired using Klenow enzyme and BamHI linkers added. The fragment is then ligated into plasmid pVL941 which has been previously digested with BamHI. The resulting plasmid is identified as pVLgag.

Cloning of gp85 Envelope Protein into Baculovirus Expression vector

The gp85 gene is removed from plasmid pTC2 by digestion with PstI enzyme. A 2 kB fragment is isolated and the ends repaired by treatment with T4 DNA polymerase followed by the addition of BamHI linkers. This BamHI fragment is ligated into the BamHI site of plasmid pVL941 which has been previously digested with BamHI. The resulting plasmid is identified as pVLgp85.

Cloning of gp70 Envelope Protein into Baculovirus Expression Vector

The gp70 portion of the env gene is produced by truncation of the gp85 gene using a synthetic oligonucleotide containing 3 in frame termination codons. This oligonucleotide is ligated into the gp85 coding sequence at the AluI site at nucleotide 7298 (*J. Virol.* 62:722–731 (1988)) and the sequences coding for the p15E protein are removed. This modified gene is ligated into the BamHI site of pVL941 (CHART C.1) to produce the plasmid pVL70.

Baculovirus Transformation

Plasmids pVLgag, pVL85 and pVL70 are cotransfected with wild type AcNPV using standard baculovirus expression vector techniques (Texas Agricultural Experimental Station Bulletin No. 1555 (1987)). Recombinant baculoviruses, AcNPV-gag, AcNPV-gp85, and AcNPV-gp70, respectively, are selected by visual screening of (−) versus (+) inclusion plaques and expression of the gag, gp85 and gp70 proteins confirmed by immunoprecipitation of $^{35}$S-methionine labelled proteins from infected Sf9 cells using monoclonal antibodies to gag or gp70, as described above.

Thus, the recombinant virus AcNPV-gag contains DNA encoding not only the gag product but, also the protease portion of the pol gene. This construct could allow for the expression of either the p65 gag precursor or a gag-protease fusion protein of 78 kD if the gag termination signals are suppressed in insect cells, as it is in a FeLV infected mammalian cells. This same gag-protease region has been inserted into the feline herpes virus (FHV) genome by Cole, G. E., et al, *J. Virol.* 64:4930–4938 (1990). This recombinant virus is shown to produce both the gag gene product and a gag-protease fusion protein in infected cells. The protease is also shown to be active in processing the gag p65 into its four polypeptide components in recombinant FHV infected cells. In addition, two forms of the envelope gene are inserted into baculovirus, a full length gene coding for the gp85 glycoprotein (recombinant virus AcNPV-gp85) and a gene which codes for only the gp70 portion of the gene (recombinant virus AcNPV-gp70). The gp70 gene product lacks the p15E portion of the gp85 glycoprotein and should be secreted into the medium of infected cells. The gp85 gene codes for a protein with a backbone of 67 kD while the gp70 gene can code for a protein with a backbone of 45 Kd.

FeLV gp70 and gp85 Expression

Immunoprecipitation of $^{35}$S-methionine labelled infected cell polypeptides shows that in AcNPV-gp85 and AcNPV-gp70 infected cells, two forms of gp85 and gp70 are synthesized and remain within the cells. EndoH treatment reduces the molecular weight of the 74 kD species in AcNPV-gp85 infected cells and the 53 Kd species in AcNPV-gp70 infected cells to that of their respective 60 Kd and 41 Kd lower molecular weight forms. Only the higher molecular weight forms of gp85 and gp70 incorporate a glucosamine label. Small amounts of gp85 and gp70 are also found in the medium of infected cells.

FeLV gag Expression and Particle Assembly

The extracellular fluid of AcNPV-gag infected Sf-9 cells is examined by sucrose gradient analysis for the presence of virus-like particles. Supernatant of the AcNPV-gag and AcNPV-gp50 infected cell high speed pellets are fractionated. AcNPV-gp50 is a recombinant virus that produces the gp50 glycoprotein gene from pseudorabies virus (PRV) and serves as a control. Both AcNPV-gag and AcNPV-gp50 have a major protein peak in the same fractions. EM analysis of these fractions shows they contain baculovirus particles. The insect cells produce particles which resemble immature FeLV particles in size (100 nm), shape, and ring structure. Only immature particles are found in the baculovirus produced material while both mature and immature particles are found in the FeLV-A/FGA supernatant preparations. Western blot analysis shows that gag expression results in the formation of virus-like particles (data not shown).

When the AcNPV-gag infected cell supernatant is gradient fractionated and analyzed by western blot, we found that several immunoreactive polypeptides are present (data not shown). This suggests that gag-pol gene product (polyprotein) are being processed and is biologically active.

Western blots of gradient fractionated FeLV particles produced by the FeLV-A/FGA cell line provide information on what the natural gp85 and gag gene products look like when fractionated under conditions identical to those used for infected insect cell supernatant. Antibody against the envelope protein reacted with a single band with a molecular weight of 80 kD. Antibody to p27 reacted with a 27 kD polypeptide in these same fractions. A large percentage of the gp70 remained near the top of the gradient which has been reported by Zelikman, I., et al, *Biotechnol. Appl. Biochem.* 11:209–216 (1989), to have been gp70 which becomes detached from the virus particle during purification.

Immunoblot analysis of gradients from cells coinfected with AcNPV-gag and AcNPV-gp85 reveal that gp85 is found just as gp70 is for FeLV. A small amount is seen at the top of the gradient, but in much lower proportion to that seen with the virus particles. When AcNPV-gp85 singly infected cell supernatant are similarly analyzed, no immunoreactive bands are seen in the gradient.

To verify the specificity of the gp85 interaction with gag, cells were co-infected with AcNPV-gag and AcNPV-gp70. Although gp70 is designed for secretion by removal of the p15E portion of the glycoprotein, very little is secreted from infected cells. If the incorporation of surface glycoproteins are random or if the 15 kD portion of the molecule are not acting as a recognition signal for gag, one would expect to find a gp70 immunoreactive polylpeptide at the same density as that of gag particles. Gp70 reactivity occurs only at the top of the gradient. No gp70 reactivity is seen at a density corresponding of virus particles (data not shown).

We also co-infected cells with AcNPV-gag and AcNPV-gp50. Gp50 is glycoprotein found on the surface of PRV and on the surface of infected cells (Ben-Porat, T., and Kaplan, A. S., *Virology* 41:265–273 (1970)). To detect gp50, a polyclonal antibody produced by vaccinating a rabbit with a recombinant vaccinia virus producing gp50 is used (*J. Virol.* 61:3977–3982 (1987)). Again no gp50 is found at the density of gag particles (data not shown), indicating that the incorporation of gp85 into the particles is specific.

Figure 1:
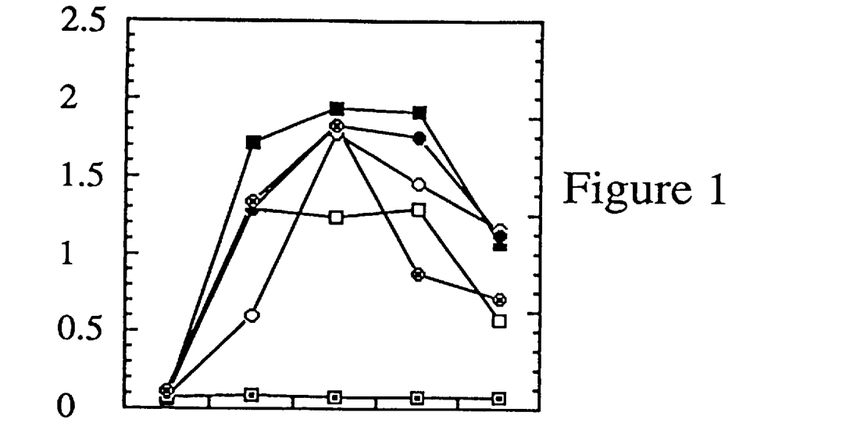
FIG. 1 illustrates the results of the p27 assay on sera taken from control group cats post challenge (Vaccine Experiment I)
Figure 2:
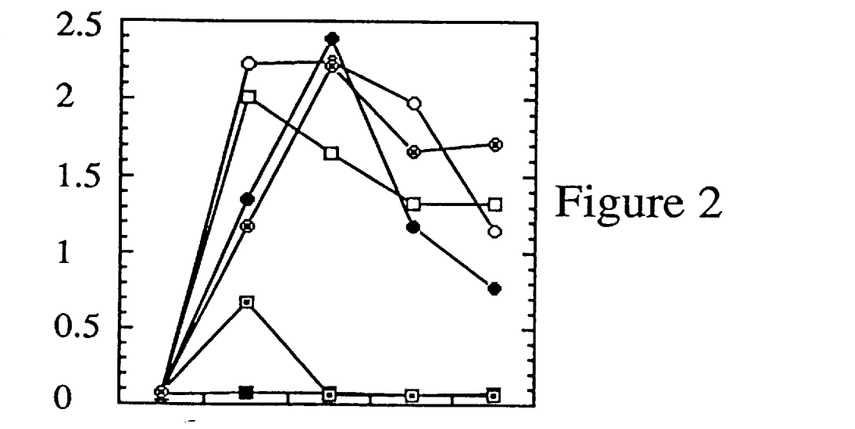
FIG. 2 illustrates the results of the p27 assay on sera taken from cats inoculated with FHVΔtkgp85 post challenge (Vaccine Experiment I)
Figure 3:
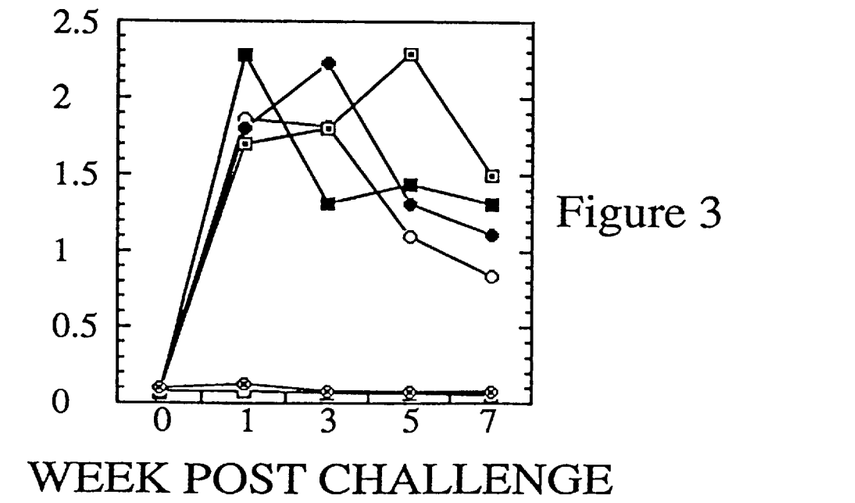
FIG. 3 illustrates the results of the p27 assay on sera taken from cats inoculated with AcNPVgp85 post challenge (Vaccine Experiment I)
Figure 4:
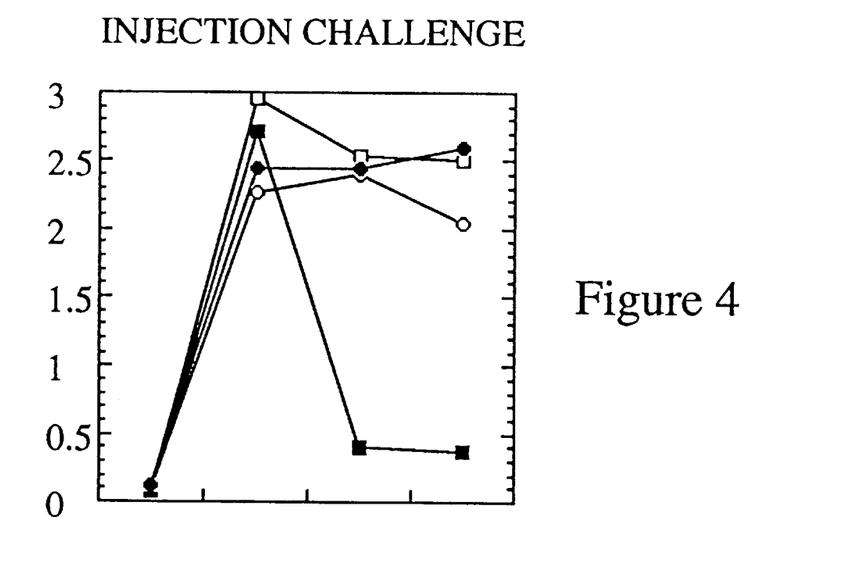
FIG. 4 illustrates the results of the p27 assay on sera taken from control group cats post injection challenge (Vaccine Experiment II)
Figure 5:
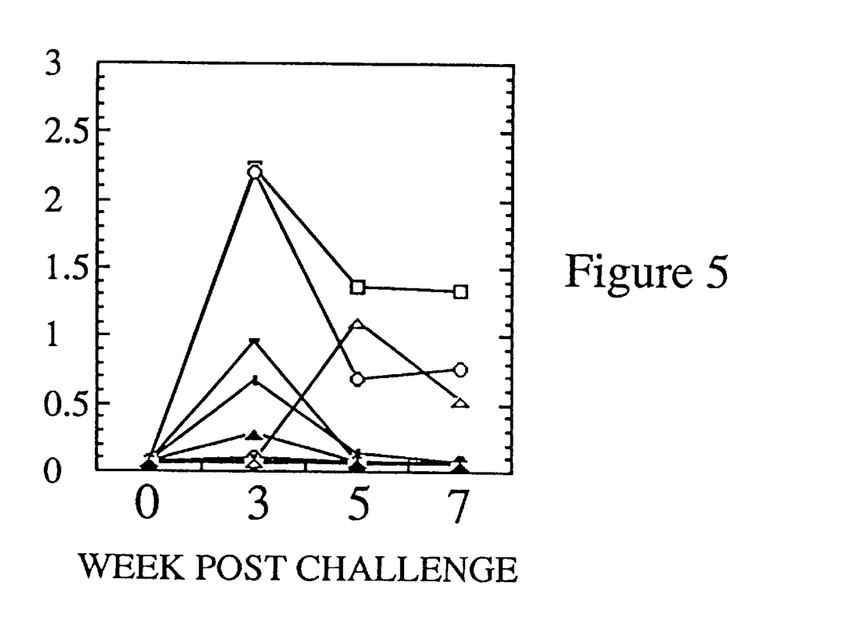
FIG. 5 illustrates the results of the p27 assay on sera taken from cats inoculated with FHVΔtkgp85 and AcNPVgp85 post injection challenge (Vaccine Experiment II)
Figure 6:
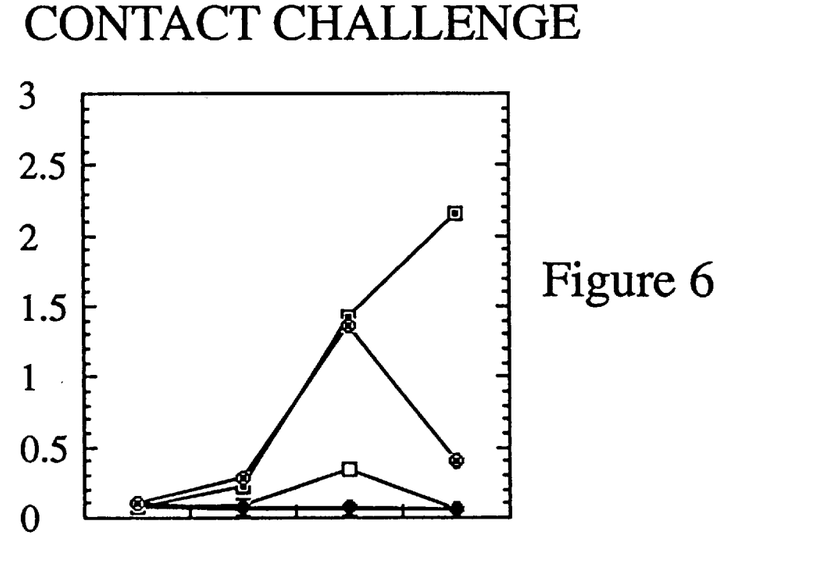
FIG. 6 illustrates the results of the p27 assay on sera taken from control group cats post contact challenge (Vaccine Experiment II)
Figure 7:
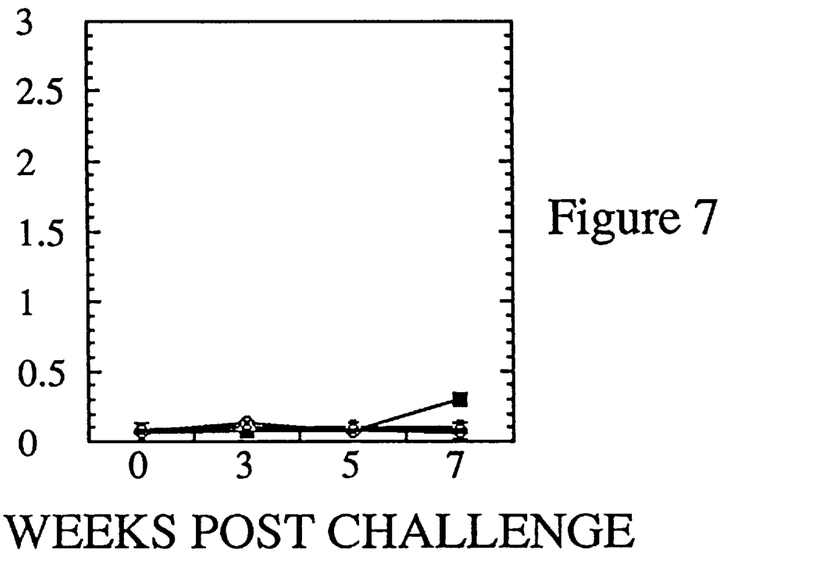
FIG. 7 illustrates the results of the p27 assay on sera taken from cats inoculated with FHV66 tkgp85 and AcNPVgp85 post contact challenge (Vaccine Experiment II)

For expression of the gp70 portion of the gp85 env gene, an oligonucleotide is designed having 3 in frame termination codons. This oligonucleotide is ligated into the gp85 coding sequence at the AluI site at nucleotide 7298 (see Donahue, P. R., et al, *J. Virol.* 62:722–731 (1988)) and the coding sequence for the p15E protein is eliminated, resulting in the production of a truncated gp70 protein. For insertion into feline herpes virus, this gp70 gene is inserted between the HCMV IE promotor and the BGH polyA signal into the FHVΔtk vector pCG113 to produce the plasmid p113-70B. This is co-transfected into Crandell Feline Kidney (CRFK) cells with DNA from FHV UT88. Recombinant viruses are isolated following the standard technique of Nunberg, J. H., et al, *Proc. Natl. Acad. Sci. USA* 81:3675–3679 (1984). Expression of the gp70 protein is confirmed by western blotting and immunoprecipitation of $^{35}$S-methionine labelled proteins from infected cells using monoclonal antibodies to gp70 (data not shown).

EXAMPLE 2

Combined Mucosal/Parenteral Vaccination

Vaccine Experiment I

Two groups of cats are used in this experiment. The first group (n=6, FIG. 2) is inoculated twice intranasally/orally (day 0 and 21) with 1.0 ml of FHVΔtkgp85 containing $1.3\times10^5$ pfu and $10^7$ pfu respectively. This is accomplished by using a syringe to which a small nasal cannula had been attached. Animals are gently restrained and approximately 0.25 ml is dropped into each nose and 0.5 ml placed towards the back of the oropharynx. The second group (n=6, FIG. 3) is inoculated intramuscularly on day 0 with $8\times10^6$ AcNPVgp85 infected Sf-9 cells and at 21 and 33 days with $10^7$ AcNPVgp85 infected Sf-9 cells. Animals are challenged intranasally/orally with 1 ml of supernatant fluid from confluent CT600 cells administered on days 0, 2, 4, and 7. On day 5, cats are immunosuppressed with Depo-Medrol (The Upjohn Company, Kalamazoo, Mich.) used at 5 mg/kg body weight. Day 0 of challenge is 40 days after the initial vaccination. Six unvaccinated cats are challenged at the same time to act as controls.

Vaccine Experiment II

A single group of animals (n=17) is used in this experiment and they are inoculated intranasally/orally with 1.0 ml of FHVΔtkgp70 containing $2\times10^5$ pfu. Twenty-seven days later, all animals are revaccinated with the same preparation. Thirty-nine days after the second vaccination, cats receive $2.5\times10^7$ Sf-9 cells infected with AcNPVgp70 via intramuscular injection. Sixty-four days after this inoculation, cats are divided into two subgroups. The first subgroup (n=10, FIG. 5) is immunosuppressed and challenged as described for Experiment 1. The second subgroup (n=7, FIG. 7) is placed in a pen with 8 persistently FeLV-infected cats and 6 unvaccinated negative controls.

Vaccine Experiment III

Seven groups of animals are used in this experiment. In the first group (n=8), cats receive two intramuscular inoculations of Sf-9 cells infected with baculovirus AcNPVgp70 at a 29-day interval. In the second group (n=8) animals receive two inoculations of Sf-9 cells. The first consisted of AcNPVgp70 and gp85/gag particles whilst the second consisted of gp85/gag particles alone. In group 3 (n=8), cats are first inoculated intranasally/orally with FHVΔtkgp85 containing $2\times10^5$ pfu in a 1 ml dose and 29 days later are intramuscularly inoculated with Sf-9 cells infected with AcNPVgp85. Cats in the fourth group (n=8) are first co-inoculated intranasally/orally with FHVΔtkgp85 and FHVΔtk gag. Each inoculation contained $2\times10^5$ pfu. Twenty-nine days later, animals receive an intramuscular inoculation of gag/gp85 particles from the supernatant collected after high speed centrifugation of infected insect cells. In group 5 (n=6), cats received two intranasal inoculations of $2\times10^5$ pfu FHVΔtkgp70, 29 days apart. In the last group, (n=8) animals are first inoculated intranasally/orally with a 1 ml dose of FHVΔtkgp70 containing $2\times10^5$ pfu. Twenty-nine days later, animals are intramuscularly inoculated with AcNPVgp70. Forty-four days after the last vaccination, all cats from each group are immunosuppressed/challenged as described in Experiment 1. Eight, matched, non-vaccinated animals are similarly challenged to act as controls.

Results of Vaccination Experiments

In Vaccine Experiment I (where cats are inoculated with either FHVΔtkgp85 or AcNPVgp85), none of the animals showed any detrimental signs to vaccination. After challenge, animals are bled and p27 levels are assayed as a measure of viraemia. FIGS. 1–3 show the results from bleeds taken before challenge and at 3, 5 and 7 weeks post-challenge. Of the 6 control cats (FIG. 1), 5 became persistently viremic and 1 never became infected. In both of the FHVΔtkgp85 (FIG. 2) and AcNPVgp85 (FIG. 3) vaccine groups, 4 of 6 animals became viremic. The levels of viraemia in animals which became infected is not different from controls. ELISA shows that none of the cats vaccinated with FHVΔtkgp85 showed a response to gp70 or whole FeLV whilst 4/6 cats vaccinated with AcNPVgp85 responded on the whole FeLV ELISA and 1/6 responded to purified gp70.

Vaccine Experiment II is designed to test 1) whether exclusion of the p15E subunit would improve efficacy, 2) whether combined mucosal and parenteral priming could enhance the vaccines protective effect and 3) whether a natural challenge system would increase the chances of detecting immunity.

The combined vaccine regime caused no detrimental signs in the animals and a large number of cats, 7/17 showed a response to gp70 compared to the previous response of the recombinant viruses given separately. A greater number, 16/17, also responded in the whole virus assay. Injection challenge established infection in 3/4 controls whilst only 3/10 vaccinated animals are p27 positive at 7 weeks (FIGS. 4 and 5). Contact challenge only established infection in 2/6 controls whilst only 1/6 vaccinates showed a very low p27 level at 7 weeks post-challenge.

These results indicate that combined mucosal/parenteral inoculation of gp70 can provide protection against challenge even in the injection/immunosuppression challenge system. The low infection rate of the controls in the contact/challenge system on the other hand make results from the vaccine/contact challenge group difficult to interpret. The protection seen in the vaccine/infection challenge group may have been due to the dual inoculation schedule or if p15E is immunosuppressive to the use of the gp70 subunit. To further probe this point and to test the importance of the gag protein in immunity, a further series of cats is vaccinated using a number of different vaccine regimes. Because of the poor infection rates established in controls using contact challenge, and the apparent success of the vaccine in the face of immunosuppression, all cats in the last experiment are challenged using the infection/immunosuppression model.

The p27 values for the six vaccine regimes at 9 weeks post challenge (Vaccine Experiment III) are shown in FIG. 8. Animals treated with gp70 in either vector alone showed some low levels of protection similar to that seen with gp85 in Vaccine Experiment I. Dual inoculation for mucosal and parenteral immunity with gp70 gave 50% protection and cats in this group which are still viremic at 9 weeks post-challenge appeared to have lower p27 levels. Dual inoculation of gp85 improved protection levels and again lowered p27 levels compared to the use of gp70. This indicates that the previously enhanced protection seen with dual site inoculation of gp70 compared to single site inoculation of gp85, is due to immunological stimulation at the two sites rather than the possible immunosuppressive effect of p15E. The inclusion of the gag protein as part of gag/gp85 particles again improved vaccine efficacy despite the fact that only a parenteral application is used. When both mucosal and parenteral sites are vaccinated using both gp85 and gag then 100% protection is achieved at 9 weeks post challenge. In this group of 8 cats, 3 animals showed a transient viraemia of between 2–4 weeks duration, whilst 5 animals never became viremic.

Antibody scores (data not shown) show that only low numbers appeared positive using the gp70 assay whilst all animals showed post-vaccination sero-conversion using the whole virus assay except cats vaccinated with FHVΔtkgp70 alone.

Vaccination Kit

A kit containing the vaccines for administration and instruction on the dual mucosal/parenteral administration of vaccines, as described herein, may be produced as a safe and cost efficient means of supplying a vaccine. The vaccination kit contains vaccines in single or multiple use vials, ampules, or other suitable containers. For mucosal administration the formulated vaccine may be in containers as previously described or in an aerosolized form. For parenteral use, a single dose syringe containing a suitable efficacious dose for the host mammal represents an easy and rapid way in which administration is accomplished. Alternatively, the kit may contain the mucosal and parenteral vaccines in multiuse vials or other suitable containers, and may be supplied ready-to-use or require some additional preparation or mixing prior to use. An instruction sheet is included which more fully describes the included vaccine(s) to be administered and their formulation, the order and timing of inoculation, as well as additional factors of concern to the practitioner.

For cats, as an example, such a vaccination kit may contain a one ml, single dose, mucosal formulation containing FHVΔtkgp85 and FHVΔtkgag ($2\times10^5$ pfu/vaccine) to be administered 0.5 ml to each nostril. The parenteral formulation includes one ml of AcNPVgp85 and AcNPVgag ($2\times10^5$ pfu/vaccine) for intramuscular administration.

For humans such a vaccination kit may contain a two ml single dose mucosal formulation containing an adenovirus/influenza virus recombinant to be administered one ml to each nostril. The parenteral formulation includes a one ml inactivated influenza virus for intramuscular administration.

For cattle such a vaccination kit may contain a five ml single dose mucosal formulation containing Bovine Herpes Type I/Bovine Viral Diarrhea Virus (BVDV)gp53 or Bovine Respiratory Syncytial Virus (BSRV) F/G to be administered 2.5 ml to each nostril. The parenteral formulation includes five ml AcNPVgp53 or AcNPVF/G for intramuscular administration.

For dogs such a vaccination kit may contain a one ml single dose mucosal formulation containing a Canine Herpes Virus/Canine Parvovirus recombinant to be administered 0.5 ml to each nostril. The parenteral formulation includes one ml of a baculovirus/Parvovirus recombinant for intramuscular administration.

For pigs such a kit may contain a two ml single dose mucosal formulation containing a PRVΔtk/Transmissible Gastroenteritis (TGE) recombinant to be administered one ml to each nostril. The parenteral formulation includes a two ml baculovirus/TGE recombinant for intramuscular administration.

We claim:

1. A multiple dose FeLV vaccination kit for a cat comprising:
   (a) a dose for parenteral administration comprising baculovirus expressed FeLV gp85 protein; and
   (b) a dose for mucosal administration comprising recombinant FHV engineered to express the DNA coding for the FeLV gp85.

2. A multiple dose FeLV vaccination kit for a cat comprising:
   (a) a dose for parenteral administration comprising baculovirus expressed FeLV gp85 and gag protein; and
   (b) a dose for mucosal administration comprising recombinant FHV engineered to express the DNA coding for the FeLV gp85 and gag genes.

3. A multiple dose FeLV vaccination kit for a cat comprising:
   (a) a dose for parenteral administration comprising baculovirus expressed FeLV gp85 and gag proteins; and
   (b) a dose for parenteral administration comprising baculovirus expressed FeLV gp85 protein, baculovirus expressed FeLV gp70 protein and baculovirus expressed FeLV gag protein.

4. A multiple dose FeLV vaccination kit for a cat comprising:
   (a) a dose comprising baculovirus expressed FeLV gp70 protein for parenteral administration;
   (b) two separate doses for mucosal administration comprising recombinant FHV engineered to express the DNA coding for the FeLV gp70 gene.

5. A method of conferring immunity to FeLV to a cat comprising:
   (a) providing a dose of baculovirus expressed FeLV gp85 protein;
   (b) providing a dose of recombinant FHV engineered to express the DNA coding for the FeLV gp85 gene;

(c) administering said dose of baculovirus expressed FeLV gp85 protein and said dose of recombinant FHV to said cat.

6. A method in accordance with claim 5, wherein said administering step comprises administration of said dose of recombinant FHV followed by administration of said dose of baculovirus expressed FeLV protein to said cat.

7. A method in accordance with claim 5, wherein said dose of recombinant FHV is administered mucosally and said dose of baculovirus expressed FeLV protein is administered parenterally to said cat.

8. A method in accordance with claim 5, wherein said administering step comprises administration of said dose of baculovirus expressed FeLV protein followed by administration of said dose of said recombinant FHV to said cat.

9. A method of conferring immunity to FeLV to a cat comprising:
   (a) providing a dose of baculovirus expressed FeLV gp85 and gag protein;
   (b) providing a dose of recombinant FHV engineered to express the DNA coding for the FeLV gp85 and gag genes;
   (c) administering said dose of baculovirus expressed FeLV gp85 and gag protein and said dose of recombinant FHV to said cat.

10. A method in accordance with claim 9, wherein said administering step comprises administration of said dose of recombinant FHV followed by administration of said dose of baculovirus expressed FeLV protein to said cat.

11. A method in accordance with claim 9, wherein said dose of recombinant FHV is administered mucosally and said dose of baculovirus expressed FeLV protein is administered parenterally to said cat.

12. A method in accordance with claim 9, wherein said administering step comprises administration of said dose of baculovirus expressed FeLV protein followed by administration of said dose of recombinant FHV to said cat.

13. A method of conferring immunity to FeLV to a cat comprising:
   (a) providing a first dose of baculovirus expressed FeLV gp85 and gag protein;
   (b) providing a second dose of baculovirus expressed FeLV gp85, gp70 and gag protein;
   (c) administering said dose of baculovirus expressed FeLV gp85 and gag protein and said dose of baculovirus expressed FeLV gp85, gp70 and gag protein to said cat.

14. A method in accordance with claim 13, wherein said administering step comprises administration of said first dose of baculovirus expressed FeLV protein followed by administration of said second dose of baculovirus expressed FeLV protein to said cat.

15. A method in accordance with claim 13, wherein said first and second doses of baculovirus expressed FeLV protein are administered parenterally to said cat.

16. A method in accordance with claim 13, wherein said administering step comprises administration of said second dose of baculovirus expressed FeLV protein followed by administration of said first dose of baculovirus expressed FeLV protein to said cat.

17. A method of conferring immunity to FeLV to a cat comprising:
   (a) providing a dose of baculovirus expressed FeLV gp70 protein;
   (b) providing a first dose of recombinant FHV engineered to express the DNA coding for the FeLV gp70 gene;
   (c) providing a second dose of recombinant FHV engineered to express the DNA coding for the FeLV gp70 gene;
   (d) administering said dose of baculovirus expressed FeLV gp70 protein and said first and second doses of recombinant FHV to said cat.

18. A method in accordance with claim 17, wherein said administering step comprises administration of said first and second doses of recombinant FHV followed by said dose of baculovirus expressed FeLV protein to said cat.

19. A method in accordance with claim 17, wherein said first and second doses of recombinant FHV are administered mucosally and said dose of baculovirus expressed FeLV protein is administered parenterally to said cat.

20. A method in accordance with claim 17, wherein said administering step comprises administration of said dose of baculovirus expressed FeLV protein followed by administration of said first and second doses of recombinant FHV to said cat.

* * * * *